(12) United States Patent
Sundermann et al.

(10) Patent No.: US 7,320,980 B2
(45) Date of Patent: Jan. 22, 2008

(54) SUBSTITUTED PYRIDO(1,2-A)PYRIMIDINES AND THEIR USE AS NOS INHIBITORS

(75) Inventors: Bernd Sundermann, Aachen (DE); Hagen-Heinrich Hennies, Simmerath (DE); Helmut Buschmann, Esplugues de Llobreget (ES); Ullvi Bluhm, Kronshagen (DE); Bernd Clement, Kiel (DE); Dieter Heber, Molfsee (DE); Ulrich Wolschendorf, Kronshagen (DE)

(73) Assignee: Gruenenthal GmbH, Aachen (DE)

( * ) Notice: Subject to any disclaimer, the term of this patent is extended or adjusted under 35 U.S.C. 154(b) by 267 days.

(21) Appl. No.: 11/218,570

(22) Filed: Sep. 6, 2005

(65) Prior Publication Data

US 2006/0084664 A1    Apr. 20, 2006

Related U.S. Application Data

(63) Continuation of application No. PCT/EP2004/002279, filed on Mar. 5, 2004.

(30) Foreign Application Priority Data

Mar. 6, 2003  (DE) ................ 103 10 106

(51) Int. Cl.
 *A61K 31/519* (2006.01)
 *C07D 471/04* (2006.01)
 *A61P 25/06* (2006.01)
(52) U.S. Cl. .................... 514/259.1; 544/282
(58) Field of Classification Search ............ 544/282; 514/259.1
 See application file for complete search history.

(56) References Cited

FOREIGN PATENT DOCUMENTS

| DE | 39 30 130 A1 | 3/1991 |
|---|---|---|
| DE | 100 50 662 A1 | 4/2002 |
| WO | WO 02/080911 A | 10/2002 |

OTHER PUBLICATIONS

Disorders Index of the National Institute of Neurological Disorders and Stroke, <http://www.ninds.nih.gov/disorders/disorder_index.htm?css=print>, downloaded Apr. 4, 2007.*
Christopherson, et al., J. Clin. Invest., vol. 100, No. 10, Nov. 1997, 2424-2429.*
Konopka, et al., Cancer Research 61, 3182-3187, Apr. 1, 2001.*
Hjorth, et al., Eur. J. Clin. Pharmacol. 2003; 59:499-505 (2 page abstract attached).*
Wolfe, et al., Ann. Pharmacother. Jan. 1995; 29(1): 36-46 (2 page abstract attached).*
Akyurek, et al., Am. J. Path., vol. 149, 1981-1990, 1996 (5 page abstract).*
Parenti, et al., FASEB. J. (Apr. 27, 2001) 10.1096/fj.00-0503fje.*
NIH website, http://www.ncbi.nlm.nih.gov/sites/entrez?cmd=Retrieve&db=PubMed&list_uids=7526964&dopt=Abstract, downloaded Jul. 19, 2007.*
NIH Medline Plus website; http://www.nlm.nih.gov/medlineplus/ency/article/000170.htm#top, downloaded Jul. 19, 2007.*
Girreser, et al., J. Prakt.Chem., 2000, 342, No. 3, pp. 230-234.*
Mayo Clinic website, http://www.mayoclinic.com/print/migraine-headache/DS00120/DSECTION=8&METHOD=print, downloaded Jul. 19, 2007.*
Medline Plus website, http://www.nlm.nih.gov/medlineplus/ency/article/000668.htm#top, downloaded Jul. 19, 2007.*
Wikipedia printout, http://en.wikipedia.org/wiki/Inflammation, downloaded Jul. 17, 2007.*
American Diabetes Assn. Website, http://www.diabetes.org/gestational-diabetes.jsp, downloaded Jul. 16, 2007.*
Kids Health website; http://www.kidshealth.org/parent/infections/lung/meningitis.html, downloaded Jul. 19, 2007.*
Ferid Murad, "Die Entdeckung Einiger Biologischer Wirkungen von Stickstoffmonoxid und Seiner Rolle für die Zellkommunikation (Nobel-Vortrag)", Angew. Chem., 1999, pp. 1976-1989, vol. 111, Wiley-VCH.
Louis J. Ignarro, "Stickstoffmonoxid: ein Einzigartiges Endogenes Signalmolekül in der Gefäßbiologie (Nobel-Vortrag)", Angew Chem., 1999, pp. 2002-2013, vol. 111, Wiley-VCH.
Harry L. Yale, „3-Benzoyl-2-Hydroxy-9-Methylpyrido [1,2-a] Pyrimdin-4-one, J. Heterocyclic Chem., (1978) pp. 1047-1049, vol. 15.
David Dubuisson, et al., "The Formalin Test: A Quantitative Study of the Analgesic Effects of Morphine, Meperidine, and Brain Stem Stimulation in Rats and Cats", Pain, (1997), pp. 161-174, Elsevier/North-Holland Biomedical Press.
Oliver H. Lowry, et al., "Protein Measurement with the Folin Phenol Reagent", May 28, 1951, pp. 265-275.
Terrence J. Coderre, et al. "Contribution of Central Neuroplasticity to Pathological Pain: Review of Clinical and Experimental Evidence", Pain, (1993), pp. 259-285, vol. 52, Elsevier Science Publishers.

(Continued)

*Primary Examiner*—Mark L. Berch
*Assistant Examiner*—Cecilia M Jaisle
(74) *Attorney, Agent, or Firm*—Crowell & Moring LLP

(57) ABSTRACT

The invention relates to substituted pyrido[1,2-a]pyrimidine compounds corresponding to formula (I)

wherein:
$R^1$, $R^2$ and $R^3$ are as defined in the specification. Related pharmaceutical formulations and methods for inhibiting nitrogen oxide synthesis (NOS) and other treatments are also provided.

32 Claims, No Drawings

OTHER PUBLICATIONS

L. H. Lassen, et al., "Nitric Oxide Synthase Inhibition on Migraine", Neuroreport, (Feb. 8, 1997), pp. 405, vol. 8.

Adrian J. Hobbs, "Inhibition of Nitric Oxide Synthase as a Potential Therapeutic Target", Annu. Rev. Pharmacol. Toxicol., (1999), pp. 191-220, vol. 39, Copyright 1999 by Annual Review.

"Nitric Oxide: from Basic Research to Clinical Applications", DDT, Feb. 1999, pp. 47-49, vol. 4, No. 2.

P.-E, et al., "Nitric Oxide Synthases: Target for Therapeutic Strategies in Neurological Diseases", CMLS, Cell. Mo. Life Sci., (1999), pp. 1029-1035, vol. 55.

Ulrich Girreser, et al., "Synthesis and Reactions of Aroyl Substituted Enone Mannich Salts [1]", J. Prakt. Chem., (2000), pp. 230-234, vol. 342, No. 3, Wiley-VCH.

Ulrich Girreser, et al., "An Efficient and Facile Synthesis of Novel 3-Benzoyl-3,4-Dihydro-2H-Pyrido [1,2-a] Pyrimidines", Letters, (Mar. 1998), pp. 263-264.

Lars Lykke Thomsen, et al., "Nitric Oxide Theory of Migraine", Clinical Neroscience, (1998), pp. 28-33, vol. 5, Wiley-Liss, Inc.

International Search report dated Jun. 6, 2004 (eight (8) pages).

German Search Report dated Nov. 25, 2003 (three sheets).

\* cited by examiner

SUBSTITUTED PYRIDO(1,2-A)PYRIMIDINES AND THEIR USE AS NOS INHIBITORS

CROSS REFERENCE TO RELATED APPLICATIONS

This application is a continuation of International Patent Application No. PCT/EP2004/002279, filed Mar. 5, 2004, designating the United States of America, and published in German as WO 2004/078755 A1, the entire disclosure of which is incorporated herein by reference. Priority is claimed based on German Patent Application No. 103 10 106.3, filed Mar. 6, 2003.

FIELD OF THE INVENTION

The present invention relates to substituted pyrido[1,2-a]pyrimidine compounds, to a process for the production thereof, to pharmaceutical preparations containing these compounds, to the use thereof for the production of pharmaceutical preparations and in related treatment methods.

BACKGROUND OF THE INVENTION

Nitrogen monoxide (NO) regulates numerous physiological processes, inter alia neurotransmission, the relaxation and proliferation of smooth muscle, the adhesion and aggregation of thrombocytes as well as tissue injury and inflammation. Due to the large number of signal functions, nitrogen monoxide has been associated with a series of diseases, for example in L. J. Ignarro, Angew. Chem. (1999), 111, pages 2002-2013 and in F. Murad, Angew. Chem. Int. Ed. (1999), 111, pages 1976-1989. Nitrogen monoxide synthase (NO synthase), the enzyme responsible for the physiological formation of nitrogen monoxide, plays an important role in influencing these diseases therapeutically. To date, three different isoforms of NO synthase have been identified, namely the two constitutive forms nNO synthase and eNO synthase together with the inducible form iNO synthase (A. J. Hobbs, A. Higgs, S. Moncada, Annu. Rev. Pharmacol. Toxicol. (1999), 39, pages 191-220; I. C. Green, P.-E. Chabrier, DDT (1999), 4, pages 47-49; P.-E. Chabrier et al., Cell. Mol. Life Sci. (1999), 55, pages 1029-1035).

The inhibition of NO synthase opens up new therapeutic approaches for various diseases which are associated with nitrogen monoxide (A. J. Hobbs et al., Annu. Rev. Pharmacol. Toxicol. (1999), 39, pages 191-220; I. C. Green, P.-E. Chabrier, DDT (1999), 4, pages 47-49; P.-E. Chabrier et al., Cell. Mol. Life Sci. (1999), 55, pages 1029-1035), such as for example migraine (L. L. Thomsen, J. Olesen, Clinical Neuroscience (1998), 5, pages 28-33; L. H. Lassen et al., The Lancet (1997), 349, 401-402), septic shock, neurodegenerative diseases such as multiple sclerosis, Parkinson's disease, Alzheimer's disease or Huntington's chorea, inflammation, inflammatory pain, cerebral ischaemia, diabetes, meningitis and arteriosclerosis. Inhibition of NO synthase may furthermore have an effect on wound healing, on tumours and on angiogenesis and bring about non-specific immunity towards microorganisms (A. J. Hobbs et al., Annu. Rev. Pharmacol. Toxicol. (1999), 39, pages 191-220).

Hitherto known active ingredients which inhibit NO synthase, apart from L-NMMA and L-NAME (i.e. L-arginine analogues from which nitrogen monoxide and citrulline are formed in vivo with the participation of NO synthase), are inter alia S-methyl-L-citrulline, aminoguanidine, S-methylisourea, 7-nitroindazole and 2-mercaptoethylguanidine (A. J. Hobbs et al., Annu. Rev. Pharmacol. Toxicol. (1999), 39, pages 191-220).

SUMMARY OF THE INVENTION

In one embodiment, an object of the present invention is to provide novel compounds, which are in particular suitable as pharmaceutical active ingredients in pharmaceutical preparations, preferably in pharmaceutical preparations for inhibiting nitrogen monoxide (NO) synthase.

The pharmaceutical preparations should moreover be suitable for the treatment or prevention of migraine, for combatting pain, in particular chronic pain and/or inflammatory pain, for the treatment of septic shock, of neurodegenerative diseases, preferably multiple sclerosis, Parkinson's disease, Alzheimer's disease and/or Huntington's chorea, inflammation, cerebral ischaemia, diabetes, meningitis, arteriosclerosis, for wound healing, for tumour treatment, for inhibiting angiogenesis or as an antibiotic or as an inhibitor for the foregoing conditions.

This object has been achieved by the provision of the substituted pyrido[1,2-a]pyrimidine compounds of the general formula I below.

The present invention accordingly provides substituted pyrido[1,2-a]pyrimidine compounds of the general formula I,

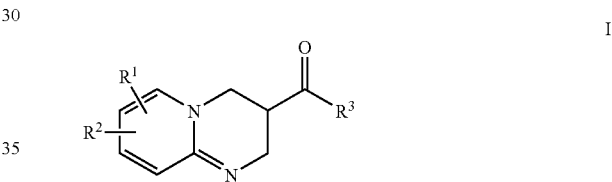

in which
$R^1$ and $R^2$, mutually independently, in each case denote hydrogen, halogen or a linear or branched, optionally at least monosubstituted alkyl residue, and
$R^3$ denotes an optionally at least monosubstituted, monocyclic aryl or heteroaryl residue, which may be fused with an optionally at least monosubstituted monocyclic or polycyclic ring system optionally comprising at least one heteroatom as a ring member,
optionally in the form of one of the pure stereoisomers thereof, in particular enantiomers or diastereomers, the racemate thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt, or in each case in the form of the solvate thereof, in particular hydrate,
wherein compounds of the general formula I, in which $R^1$ and $R^2$ denote hydrogen and a methyl residue or $R^1$ and $R^2$ in each case denote hydrogen and $R^3$ in each case denotes a phenyl residue which is unsubstituted or monosubstituted with a methyl residue, methoxy residue, Cl or Br together with the compounds
(3,4-dihydro-9-methyl-2H-pyrido[1,2-a]pyrimidin-3-yl)(3,4-dimethoxyphenyl)-methanone,
(3,4-dihydro-6-methyl-2H-pyrido[1,2-a]pyrimidin-3-yl)(3,4-dimethoxyphenyl)-methanone, (3,4-dihydro-2H-pyrido[1,2-a]pyrimidin-3-yl)(3,4-dimethoxyphenyl)-methanone and
(3,4-dichlorophenyl)(3,5-dihydro-2H-pyrido[1,2-a]pyrimidin-3-yl)-methanone and in each case the hydroperchlorate salts thereof are excepted.

For the purposes of the present invention, a mono-, di-, tri- or polycyclic ring system is taken to mean mono-, di-, tri- or polycyclic hydrocarbon residues, which may be saturated, unsaturated or aromatic. If a di-, tri- or polycyclic ring system is present, it may also comprise in different rings two or more corresponding substructures exhibiting a different degree of saturation. The mono-, di-, tri- or polycyclic ring system may optionally also comprise one or more heteroatoms as ring members, wherein the rings may in each case comprise identical or different heteroatoms. If a di-, tri- or polycyclic ring system is present, the individual rings thereof are preferably fused with one another.

The person skilled in the art will understand that in general formula I, and likewise in the general formula II below, the two residues $R^1$ and $R^2$ may be attached to any of the four possible positions of the corresponding ring.

Preferred substituted pyrido[1,2-a]pyrimidine compounds of the above general formula I are those in which the residues $R^1$ and $R^2$, mutually independently, in each case denote H, F, Cl, Br or a linear or branched, optionally at least monosubstituted $C_{1-6}$ alkyl residue, preferably H or a methyl residue, and $R^3$ has the above-stated meaning, optionally in the form of one of the pure stereoisomers thereof, in particular enantiomers or diastereomers, the racemate thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt, or in each case in the form of the solvate thereof, in particular hydrate.

Further preferred substituted pyrido[1,2-a]pyrimidine compounds of the above general formula I are those in which the residue $R^3$ denotes an optionally at least monosubstituted, 5- or 6-membered, monocyclic aryl or heteroaryl residue, which may be fused with an optionally at least monosubstituted mono-, di- or tricyclic ring system optionally comprising at least one heteroatom as a ring member, wherein the rings of the ring system are in each case 5- to 7-membered, preferably an at least monosubstituted phenyl residue or an optionally at least monosubstituted phenyl, naphthyl, furanyl, thiophenyl, pyrrolyl, imidazolyl, pyrazolyl, pyridinyl, pyrimidinyl, quinolinyl or isoquinolinyl residue, and the residues $R^1$ and $R^2$ in each case have the above-stated meaning, optionally in the form of one of the pure stereoisomers thereof, in particular enantiomers or diastereomers, the racemate thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt, or in each case in the form of the solvate thereof, in particular hydrate.

If $R^1$ and/or $R^2$ of the above general formula I denotes an at least monosubstituted, branched or unbranched alkyl residue, the substituents thereof may in each case preferably be selected from the group consisting of halogen and hydroxy, particularly preferably from the group consisting of F, Cl, Br and OH. If an alkyl residue is polysubstituted, the substituents may be identical or different.

If $R^3$ in the above general formula I denotes an at least monosubstituted, monocyclic aryl or heteroaryl residue and/or comprises an at least monosubstituted, mono- or polycyclic ring system, the corresponding substituents thereof may, in each case mutually independently, preferably be selected from the group consisting of halogen, $C_{1-4}$ alkoxy, $C_{1-4}$ alkyl, unsubstituted phenyl and at least monosubstituted phenyl, preferably from the group consisting of F, Cl, Br, methoxy, ethoxy, methyl and unsubstituted phenyl. If the phenyl substituent is itself mono- or polysubstituted, the substituents thereof may in each case preferably be selected from the group consisting of F, Cl, Br and methoxy.

If $R^3$ in the above general formula I denotes a heteroaryl residue and/or comprises a monocyclic or polycyclic ring system containing at least one heteroatom as a ring member, the heteroatom or heteroatoms may, unless otherwise stated, in each case mutually independently preferably be selected from the group consisting of nitrogen, oxygen and sulfur.

Particularly preferred substituted pyrido[1,2-a]pyrimidine compounds of the above general formula I are those selected from the group consisting of:

3-(2'-naphthoyl)-3,4-dihydro-2H-8-methylpyrido[1,2-a]pyrimidine, 3-(2'-naphthoyl)-3,4-dihydro-2H-6,8-dimethylpyrido[1,2-a]pyrimidine, 3-(4'-fluorobenzoyl)-3,4-dihydro-2H-8-methylpyrido[1,2-a]pyrimidine, 3-benzoyl-3,4-dihydro-2H-6,8-dimethylpyrido[1,2-a]pyrimidine, 3-(4'-biphenylcarbonyl)-3,4-dihydro-2H-8-methylpyrido[1,2-a]pyrimidine, 3-(4'-biphenylcarbonyl)-3,4-dihydro-2H-6-methylpyrido[1,2-a]pyrimidine, (4-ethoxy-phenyl)-(8-methyl-3,4-dihydro-2H-pyrido[1,2-a]pyrimidin-3-yl)-methanone, biphenyl-4-yl-(6,8-dimethyl-3,4-dihydro-2H-pyrido[1,2-a]pyrimidin-3-yl)-methanone, (8-methyl-3,4-dihydro-2H-pyrido[1,2-a]pyrimidin-3-yl)-(6-methyl-naphthalen-2-yl)-methanone, and (6-methoxy-naphthalen-2-yl)-(8-methyl-3,4-dihydro-2H-pyrido[1,2-a]pyrimidin-3-yl)-methanone, optionally in the form of the free base thereof or in the form of the physiologically acceptable salt thereof, in particular hydroperchlorate salt, or in each case in the form of the solvate thereof, in particular hydrate.

The present invention also provides a process for the production of substituted pyrido[1,2-a]pyrimidine compounds of the above general formula I according to the invention, in which at least one compound of the general formula III,

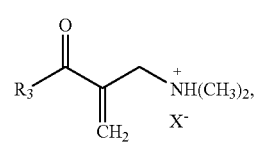

in which $R^3$ has the above meaning and $X^-$ denotes a chloride or bromide anion, is reacted with at least one compound of the general formula IV,

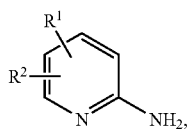

in which $R^1$ and $R^2$ have the above meaning, in a suitable reaction medium, preferably in a water/alcohol mixture, particularly preferably in a water/ethanol mixture, with heating, preferably with refluxing, and the resultant compound of the general formula I is optionally purified using conventional methods known to the person skilled in the art and optionally isolated.

The compounds of the general formulae III and IV are commercially obtainable or may be prepared using conventional methods known to the person skilled in the art, as for example described in U. Girreser et al., Synlett 1998, pages 263 et seq. and in Heber, D., Girreser, U., J. Prakt. Chem., 2000, 342, no. 3, pages 230-234. Production of the above-excepted compounds may proceed in a manner similar to the process according to the invention and is likewise described in the above-stated literature. The corresponding literature descriptions are hereby introduced as a reference and are deemed to be part of the disclosure.

It has surprisingly now been found that the substituted pyrido[1,2-a]pyrimidine compounds of the above general formula I, including the above-excepted compounds, act as inhibitors on nitrogen monoxide synthase (NO synthase) and are in particular suitable for combatting pain, preferably chronic pain and/or inflammatory pain, for the prevention and/or treatment of migraine, for the treatment of septic shock, neurodegenerative diseases, preferably multiple sclerosis, Parkinson's disease, Alzheimer's disease and/or Huntington's chorea, inflammation, cerebral ischaemia, diabetes, meningitis, arteriosclerosis, for wound healing, for tumour treatment, for inhibiting angiogenesis and as an antibiotic, preferably by triggering a nonspecific immune response against microorganisms.

The present invention accordingly provides a pharmaceutical preparation containing at least one substituted pyrido[1,2-a]pyrimidine compound of the general formula II,

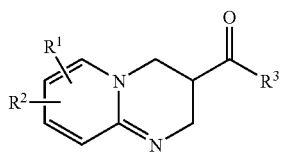

in which
$R^1$ and $R^2$, mutually independently, in each case denote hydrogen, halogen or a linear or branched, optionally at least monosubstituted alkyl residue, and
$R^3$ denotes an optionally at least monosubstituted, monocyclic aryl or heteroaryl residue, which may be fused with an optionally at least monosubstituted monocyclic or polycyclic ring system optionally comprising at least one heteroatom as a ring member,
optionally in the form of one of the pure stereoisomers thereof, in particular enantiomers or diastereomers, the racemate thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt, or in each case in the form of the solvate thereof, in particular hydrate.

Preferred pharmaceutical preparations are those containing at least one substituted pyrido[1,2-a]pyrimidine compound of the above general formula II, in which the residues $R^1$ and $R^2$, mutually independently, in each case denote H, F, Cl, Br or a linear or branched, optionally at least monosubstituted $C_{1-6}$ alkyl residue, preferably H or methyl, and $R^3$ has the above-stated meaning, optionally in the form of one of the pure stereoisomers thereof, in particular enantiomers or diastereomers, the racemate thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt, or in each case in the form of the solvate thereof, in particular hydrate.

Further preferred pharmaceutical preparations are those containing at least one substituted pyrido[1,2-a]pyrimidine compound of the above general formula II, in which $R^3$ denotes an optionally at least monosubstituted, 5- or 6-membered, monocyclic aryl or heteroaryl residue, which may be fused with an optionally at least monosubstituted mono-, di- or tricyclic ring system optionally comprising at least one heteroatom as a ring member, wherein the rings of the ring system are in each case 5- to 7-membered, preferably an optionally at least monosubstituted phenyl, naphthyl, furanyl, thiophenyl, pyrrolyl, imidazolyl, pyrazolyl, pyridinyl, pyrimidinyl, quinolinyl or isoquinolinyl residue, particularly preferably an optionally at least monosubstituted phenyl or naphthyl residue, and $R^1$ and $R^2$ in each case have the above-stated meaning, optionally in the form of one of the pure stereoisomers thereof, in particular enantiomers or diastereomers, the racemate thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt, or in each case in the form of the solvate thereof, in particular hydrate.

If $R^1$ and/or $R^2$ of the above general formula II denote an at least monosubstituted, branched or unbranched alkyl residue, the substituents thereof may in each case preferably be selected from the group consisting of halogen and hydroxy, particularly preferably from the group consisting of F, Cl, Br and OH. If an alkyl residue is polysubstituted, the substituents may be identical or different.

If $R^3$ in the above general formula II denotes an at least monosubstituted, monocyclic aryl or heteroaryl residue and/or comprises an at least monosubstituted, mono- or polycyclic ring system, the corresponding substituents thereof may, in each case mutually independently, preferably be selected from the group consisting of halogen, $C_{1-4}$ alkoxy, $C_{1-4}$ alkyl, unsubstituted phenyl and at least monosubstituted phenyl, preferably from the group consisting of F, Cl, Br, methoxy, ethoxy, methyl and unsubstituted phenyl. If the phenyl substituent is itself mono- or polysubstituted, the substituents thereof may in each case preferably be selected from the group consisting of F, Cl, Br and methoxy.

If $R^3$ in the above general formula II denotes a heteroaryl residue and/or comprises a monocyclic or polycyclic ring system containing at least one heteroatom as a ring member, the heteroatom or heteroatoms may, unless otherwise stated, in each case mutually independently preferably be selected from the group consisting of nitrogen, oxygen and sulfur.

Particularly preferred pharmaceutical preparations are those containing at least one substituted pyrido[1,2-a]pyrimidine compound of the general formula II, selected from the group consisting of:
3-(2'-naphthoyl)-3,4-dihydro-2H-8-methylpyrido[1,2-a]pyrimidine,
3-(2'-naphthoyl)-3,4-dihydro-2H-6,8-dimethylpyrido[1,2-a]pyrimidine,
3-(4'-fluorobenzoyl)-3,4-dihydro-2H-8-methylpyrido[1,2-a]pyrimidine,
3-benzoyl-3,4-dihydro-2H-6,8-dimethylpyrido[1,2-a]pyrimidine,
3-(4'-biphenylcarbonyl)-3,4-dihydro-2H-8-methylpyrido[1,2-a]pyrimidine,
3-(4'-biphenylcarbonyl)-3,4-dihydro-2H-6-methylpyrido[1,2-a]pyrimidine,
3-(4'-bromobenzoyl)-3,4-dihydro-2H-8-methylpyrido[1,2-a]pyrimidine,
3-(4'-chlorobenzoyl)-3,4-dihydro-2H-8-methylpyrido[1,2-a]pyrimidine,
3-benzoyl-3,4-dihydro-2H-8-methylpyrido[1,2-a]pyrimidine,
(4-ethoxy-phenyl)-(8-methyl-3,4-dihydro-2H-pyrido[1,2-a]pyrimidin-3-yl)-methanone,
biphenyl-4-yl-(6,8-dimethyl-3,4-dihydro-2H-pyrido[1,2-a]pyrimidin-3-yl)-methanone,
(8-methyl-3,4-dihydro-2H-pyrido[1,2-a]pyrimidin-3-yl)-(6-methyl-naphthalen-2-yl)-methanone, and
(6-methoxy-naphthalen-2-yl)-(8-methyl-3,4-dihydro-2H-pyrido[1,2-a]pyrimidin-3-yl)-methanone,
optionally in the form of the free base thereof or in the form of the physiologically acceptable salt thereof, in particular hydroperchlorate salt, or in each case in the form of the solvate thereof, in particular hydrate.

The present invention also provides the use of at least one substituted pyrido[1,2-a]pyrimidine compound of the above general formula II, optionally in the form of one of the pure stereoisomers thereof, in particular enantiomers or diastereomers, the racemate thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt, or in each case in the form of the solvate thereof, in particular hydrate, for the production of a pharmaceutical preparation for inhibiting nitrogen monoxide synthase, for combatting pain, preferably chronic pain and/or inflammatory pain, for the prevention and/or treatment of migraine, for the treatment of septic shock, neurodegenerative diseases, preferably multiple sclerosis, Parkinson's disease, Alzheimer's disease and/or Huntington's chorea, inflammation, cerebral ischaemia, diabetes, meningitis, arteriosclerosis, for wound healing, for tumour treatment, for inhibiting angiogenesis and as an antibiotic, preferably by triggering a nonspecific immune response against microorganisms.

The substituted pyrido[1,2-a]pyrimidine compounds of the above general formulae I and II and optionally in each case corresponding stereoisomers may be obtained using conventional methods known to the person skilled in the art in the form of the physiologically acceptable salts thereof, wherein the pharmaceutical preparation according to the invention may comprise one or more salts of one or more of these compounds.

The physiologically acceptable salts of the substituted pyrido[1,2-a]pyrimidine compounds of the above general formulae I and II may be obtained, for example, by reaction with one or more inorganic or organic acids, preferably selected from the group consisting of perchloric acid, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharic acid, cyclohexanesulfamic acid, aspartame, monomethylsebacic acid, 5-oxoproline, hexane-1-sulfonic acid, nicotinic acid, 2-aminobenzoic acid, 3-aminobenzoic acid or 4-aminobenzoic acid, 2,4,6-trimethylbenzoic acid, α-lipoic acid, acetylglycine, acetylsalicylic acid, hippuric acid and aspartic acid.

The preferred salt is the corresponding hydroperchlorate salt, which may preferably be obtained by dissolving the particular substituted pyrido[1,2-a]pyrimidine compound of the above general formula I or II or a corresponding stereoisomer in a suitable organic solvent, such as for example isopropanol, and converting it with perchloric acid and water into the corresponding hydroperchlorate salt.

The substituted pyrido[1,2-a]pyrimidine compounds of the above general formulae I and II and optionally corresponding stereoisomers and in each case the physiologically acceptable salts thereof may be obtained in the form of the solvates thereof, in particular hydrates, using conventional methods known to the person skilled in the art.

If the substituted pyrido[1,2-a]pyrimidine compounds of the above general formulae I and II are obtained after the production thereof in the form of a mixture of the stereoisomers thereof, preferably in the form of the racemates thereof or other mixtures of their various enantiomers and/or diastereomers, these may be separated and optionally isolated by conventional methods known to the person skilled in the art. Examples which may be mentioned are chromatographic separation methods, in particular liquid chromatography methods at standard pressure or at elevated pressure, preferably MPLC and HPLC methods, and fractional crystallisation methods. Individual enantiomers, for example diastereomeric salts formed by means of HPLC on a chiral phase or by means of crystallisation with chiral acids, for instance (+)-tartaric acid, (−)-tartaric acid or (+)-10-camphorsulfonic acid, may here in particular be separated from one another.

The substituted pyrido[1,2-a]pyrimidine compounds of the above general formulae I and II and optionally corresponding stereoisomers and in each case the corresponding salts and solvates are toxicologically safe and are thus suitable as pharmaceutical active ingredients in pharmaceutical preparations.

The pharmaceutical preparation according to the invention may be formulated as a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally pressed into tablets, packaged in capsules or suspended in a liquid, and may also be administered as such.

Apart from one or more of the substituted pyrido[1,2-a]pyrimidine compounds of the above general formula II, optionally in the form of one of the pure stereoisomers thereof, in particular enantiomers or diastereomers, the racemates thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt, or in each case in the form of the solvate thereof, in particular hydrate, the pharmaceutical preparation according to the invention conventionally contains further physiologically acceptable pharmaceutical auxiliary substances, which may preferably be selected from the group consisting of matrix materials, fillers, solvents, diluents, surface-active substances, dyes, preservatives, disintegrants, slip agents, lubricants, aromas and binders.

The physiologically acceptable auxiliary substances selected and the quantities thereof to be used depend on whether the pharmaceutical preparation is to be administered orally, subcutaneously, parenterally, intravenously, intraperitoneally, intradermally, intramuscularly, intranasally, buccally, rectally or topically, for example onto infections of the skin, the mucous membranes and the eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

The substituted pyrido[1,2-a]pyrimidine compounds of the above general formula II used in the pharmaceutical preparations according to the invention, optionally in the form of one of the pure stereoisomers thereof, in particular enantiomers or diastereomers, the racemates thereof or in the form of a mixture of stereoisomers, in particular the enantiomers or diastereomers, in any desired mixing ratio, or in each case in the form of the free base thereof or in the form of physiologically acceptable salt thereof, in particular hydroperchlorate salt or in each case in the form of the solvate thereof, in particular hydrate, in a depot in dissolved form or in a dressing, optionally with the addition of skin penetration promoters, are suitable percutaneous administration preparations.

Orally or percutaneously administrable formulations may also release the particular substituted pyrido[1,2-a]pyrimidine compounds of the above general formula II, optionally in the form of one of the pure stereoisomers thereof, in particular enantiomers or diastereomers, the racemates thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt, or in each case in the form of the solvate thereof, in particular hydrate, in delayed manner.

The quantity the particular substituted pyrido[1,2-a]pyrimidine compound of the above general formula II, optionally in the form of one of the pure stereoisomers thereof, in particular enantiomers or diastereomers, the racemate thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt, or in each case in the form of the solvate thereof, in particular hydrate, to be administered to patients may vary and is for example dependent on the weight or age of the patient and on the mode of administration, the indication and the severity of the complaint. Conventionally, 0.005 to 500 mg/kg, preferably 0.05 to 5 mg/kg of patient body weight of at least one substituted pyrido[1,2-a]pyrimidine compound of the above general formula II is administered, optionally in the form of one of the pure stereoisomers thereof, in particular enantiomers or diastereomers, the racemates thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt, or in each case in the form of the solvate thereof, in particular hydrate.

Pharmacological Methods

The assays used for determining the inhibition of nitrogen monoxide synthase by the compounds of the general formula II used according to the invention are described below.

(a) Nitrogen Monoxide Synthase (NOS) Assay

This assay makes it possible to determine the percentage inhibition of NO synthase (hereinafter referred to as the enzyme) by a compound of the general formula II used according to the invention, optionally in the form of one of the pure stereoisomers thereof, in particular enantiomers or diastereomers, the racemates thereof or in the form of a mixture of stereoisomers, in particular the enantiomers or diastereomers, in any desired mixing ratio, or in each case in the form of the free base thereof or in the form of the physiologically acceptable salt thereof, in particular hydroperchlorate salt or in each case in the form of the solvate thereof, in particular hydrate (hereinafter referred to as the active ingredient), by measuring enzyme activity on exposure to the compound. The enzyme is here mixed under suitable conditions together with radioactively labelled arginine and the particular active ingredient. After termination of the NO formation reaction at a predetermined time, the quantity of unconverted arginine is directly or indirectly determined. Comparing this quantity with the quantity of arginine remaining in the mixture of enzyme and arginine without addition of active ingredient and under otherwise identical conditions reveals the percentage inhibition of the enzyme by the active ingredient under test.

This assay may be carried out as follows:
(a) Incubation of the enzyme with labelled arginine as the substrate in a reaction vessel,
(b) Separation of the labelled arginine from the labelled citrulline optionally arising as a product of the enzymatic reaction at a time at which the concentration of citrulline is rising,
(c) Measurement of the quantity of arginine separated in each case.

Separation is performed by means of a filter plate membrane.

This assay is in particular suitable for "High Throughput Screening" (HTS) on microtitre plates (MTP).

(b) HTS (High-Throughput-Screening) NOS Assay:

Radioactive arginine is used as the substrate in this HTS-NOS assay. Depending on the type of microtitre plate (MTP), the assay volume may be selected in the range between 25 µl and 250 µl. Depending on the enzyme source used, cofactors and coenzymes are added. The batches are incubated in this microtitre plate (assay MTP) according to step (a) at room temperature and, depending on the enzyme activity used (units), lasts between 5 and 60 minutes. On completion of incubation (step (a)), the plate is placed in a cell harvester, which is equipped with an MTP which has a cation exchange membrane as a filter bottom (filter MTP). All the batches from the assay MTP are transferred into this filter MTP and suction filtered through a cation exchange filter plate, a paper filter loaded with phosphate groups. The filter MTP is then washed with buffer or water. This procedure binds the remaining substrate arginine onto the cation exchanger, while the enzymatically formed radioactive citrulline is quantitatively eluted. Once the filter MTP has been dried and scintillation liquid (Ready Protein, Beckmann Coulter GmbH, Krefeld, Germany) added, the bound arginine can be counted in the scintillation counter (Packard TRI-CARB Liquid Scintillation Analyzer 2000 CA, Packard Instrument, Meriden, Conn. 06450, USA). Low radioactivity indicates an uninhibited enzyme reaction. An inhibited enzyme reaction means that the radioactive argingine has not been converted. It may be concluded from this that there is then a high level of radioactivity on the filter.

(c) Formaldehyde Test (Rat)

The investigations for determining the antinociceptive action of the compounds used according to the invention of the general formula II were carried out by the formaldehyde test on male rats (Sprague-Dawley, 150-170 g, Charles River).

In the formaldehyde test, a distinction is drawn between the first (early) phase (0-15 min after formaldehyde injection) and the second (later) phase (15-60 min after formaldehyde injection), as described in D. Dubuisson, S. G. Dennis, Pain 4, 161-174 (1977). The early phase, being a direct response to the formaldehyde injection, is considered to be a model for acute pain, while the late phase is considered to be a model for persistent (chronic) pain, as described in T. J. Coderre, J. Katz, A. L. Vaccarino, R. Melzack, Pain, vol. 52, p. 259, 1993. The corresponding literature descriptions are hereby introduced as a reference and are deemed to be part of the disclosure.

The compounds used according to the invention of the general formula II were investigated in the second phase of the formaldehyde test in order to obtain information regarding the action of the substances in chronic/inflammatory pain.

A nociceptive reaction was induced in the freely mobile test animals by a single, subcutaneous formaldehyde injection (50 µl, 5 wt. %) into the dorsal side of the rear hind paw, the reaction being classed according to one of the following behavioural parameters: lifting and holding up the affected paw (score 1), shaking or twitching (score 2), licking and biting (score 3). The differential behaviour induced by the formaldehyde injection was recorded by observing the rats in the late phase of the formaldehyde test and assigned a variable weighting in the evaluation. Normal behaviour, in which the rat places an even load on all four paws, was recorded as a score of 0. The time of administration before the formaldehyde injection was selected as a function of the mode of administration of the compounds of the general formula II (intraperitoneal: 15 min; intravenous: 5 min). After injection of the substances, which are antinociceptively active in the formaldehyde test, the described behaviours (score 1-3) of the animals are reduced or even eliminated. A comparison was made with control animals which had received vehicle (solvent) before administration of the formaldehyde. The nociceptive behaviour was calculated as a "pain rate" (PR). The various behavioural parameters were differently weighted (factor of 0, 1, 2, 3). The calculation was carried out in accordance with the following equation at sub-intervals of 3 min:

$$PR=[(T_0\times 0)+(T_1\times 1)+(T_2\times 2)+(T_3\times 3)]/180,$$

wherein $T_0$, $T_1$, $T_2$, and $T_3$ in each case correspond to the time in seconds for which the animal exhibited behaviour 0, 1, 2 or 3. The active ingredient and vehicle groups in each case comprise n=10 animals. On the basis of the calculated PR values, the effect of the compounds of the general formula II used according to the invention was determined as a percentage change relative to the control. The $ED_{50}$ calculations were carried out by regression analysis.

The invention is explained below with reference to Examples. These explanations are given merely by way of example and do not restrict the general concept of the invention.

EXAMPLES

The chemicals and solvents used were purchased from the usual manufacturers (for example Fluka, Merck, Acros).

The NMR spectra were measured with spectrometers made by Bruker Analytik GmbH, Silberstreifen 4, D-76287 Rheinstetten. The instrument names are as follows: for 300 MHz: Avance DPX 300 MHz, for 600 MHz: Avance DRX 600 MHz.

The ESI mass spectra were measured with a Finnigan LCQ model instrument made by Thermoquest (Analytische Systeme GmbH, Boschring 12, D-63329 Egelsbach) and evaluated with Xcalibur software.

Example 1

3-(2'-Naphthoyl)-3,4-dihydro-2H-8-methylpyrido[1,2-a]pyrimidinium perchlorate 1 mmol (255 mg) of 1-(2'-naphthyl)-2-(dimethylaminomethyl)prop-2-en-1-one hydrochloride and 1 mmol (108 mg) of 2-amino-4-methylpyridine (2-amino-4-picoline) were dissolved in 15 ml of water/ethanol (1:1 volume/volume) and refluxed for 1 hour. The solvent was removed under a vacuum (bath temperature 50° C.), the resultant residue was dissolved in 20 ml of 2-propanol, combined with cooling (ice/water/common salt) with 4 mmol of 70 vol. % perchloric acid and stirred for 30 min at 0 to –10° C. The resultant precipitate was removed by suction filtration and refluxed for 30 min in 10 ml of 2-propanol. The precipitate subsequently obtained on cooling was filtered, recrystallised from methanol and dried at 60° C. under an oil pump vacuum.

Yield: 217 mg (0.54 mmol) 54% of theoretical, light yellow crystals,

Melting point: 186° C.

$C_{20}H_{19}N_2O_5Cl$ (402.83)

Calculated: C 59.63; H 4.75; N 6.96

Found: C 59.61; H 4.85; N 6.90

$^1$H-NMR (300 MHz, DMSO-$d_6$):

δ/ppm (TMS)=2.32 (s, br, 3H, $CH_3$), 3.62 (mc, 1H, H-2/4), 3.84 (d, 1H, $^2J$=13.9, H-2/4), 4.41-4.61 (m, 3H, H-3, H-2/4), 6.74 (d, 1H, $^2J$=6.9, ArH), 6.81 (s, 1H, ArH), 7.69 (mc, 2H, ArH), 7.92 (d, 1 H, $^3J$=6.9, ArH), 7.99-8.15 (m, 5H, ArH), 8.86 (s, 1H, ArH), 9.31 (s, br, NH).

MS (EI, MeOH):

m/z (%)=302 ($M^+$ of the base, 21), 301 ($M^+$–1, 14), 285 (3), 271 (2), 259 (2), 233 (2), 210 (11), 194 (7), 182 (4), 172 (7), 155 (20), 147 ($M^+$–2'-naphthoyl, 100), 127 (41), 121 (14), 109 (31), 92 (26), 77 (9), 65 (18), 44 (24).

Example 2

3-(2'-Naphthoyl)-3,4-dihydro-2H-6,8-dimethylpyrido[1,2-a]pyrimidinium perchlorate 1 mmol (255 mg) of 1-(2'-naphthyl)-2-(dimethylaminomethyl)prop-2-en-1-one hydrochloride and 1 mmol (122 mg) of 2-amino-4,6-dimethylpyridine were dissolved in 5 ml of water/ethanol (1:1 volume/volume) and refluxed for 1.5 hours. The solvent was removed under a vacuum (bath temperature 50° C.), the residue dissolved in 5 ml of 2-propanol, precipitated with cooling (ice/water/common salt) with a mixture of 70 vol. % perchloric acid and 2-propanol (1:1 volume/volume) and stirred for 30 min in the ice bath. The resultant light yellow precipitate was removed by suction filtration, washed with a little 2-propanol and dried under an oil pump vacuum (24 hours, 40° C.).

Yield: 150 mg (0.36 mmol), 36% of theoretical, light yellow crystals, $C_{21}H_{21}N_2O_5Cl$ (416.86)

$^1$H-NMR (300 MHz, DMSO-$d_6$):

δ/ppm (TMS)=2.5* (s, br, 3H, $CH_3$), 3.42-3.65 (m, 1H, H-2/4), 3.75-3.85 (m, 1H, H-2/4), 4.32-4.55 (m, 3H, H-3, H-2/4), 6.70 (s, 1H, ArH, H-7/9), 6.76 (s, 1H, ArH, H-7/9), 7.72 (mc, 2H, ArH), 7.99-8.17 (m, 4H, ArH), 8.90 (s, 1H, ArH), 9.54 (s, br, NH).

(*) masked by DMSO signal.

Example 3

3-(4'-Bromobenzoyl)-3,4-dihydro-2H-8-methylpyrido[1,2-a]pyrimidinium perchlorate 1 mmol (305 mg) of 1-(4'-bromophenyl)-2-(dimethylaminomethyl)prop-2-en-1-one hydrochloride and 1 mmol (108 mg) of 2-amino-4-methylpyridine (2-amino-4-picoline) were dissolved in 5-10 ml of water/ethanol (1:1 volume/volume) and refluxed for 1 hour. The solvent was removed under a vacuum (bath temperature 50° C.), the residue dissolved in 10 ml of 2-propanol, combined with cooling with 4 mmol of 70 vol. % perchloric acid and stirred for 30 min in the ice bath and the solvent removed under a vacuum. The oily residue was stirred with a little ethanol for 1 hour at 0° C. and the resultant colourless precipitate was removed by suction filtration and dried under an oil pump vacuum at 60° C.

Yield: 198 mg (0.46 mmol), 46% of theoretical, colourless crystals,

Melting point: 158-161° C.

$C_{16}H_{16}N_2O_5BrCl$ (431.67)

Calculated: C 44.52; H 3.74; N 6.49

Found: C 44.48; H 3.83; N 6.39

$^1$H-NMR (300 MHz, DMSO-$d_6$):

δ/ppm (TMS)=2.31 (s, 3H, $CH_3$), 3.51 (mc, 1H, H-2/4), 3.75 (d, 1H, $^2J$=12.6, H-2/4), 4.35-4.51 (m, 3H, H-3, H-2/4), 6.72-6.76 (m, 2H, H-7/9), 7.81 (d, 2H, $^3J$=8.7, H-3'/5'), 7.91 (d, 1H, $^3J$=6.8, H-6), 7.98 (d, 2H, $^3J$=8.7, H-2'/6'), 9.20 (s, br, NH).

MS (EI, MeOH):

m/z (%)=332/330 ($M^+$ of the base, 6), 330/328 ($M^+$−1, 11), 315 (2), 287 (2), 262/260 (1), 240/238 (1), 202/200 (6), 185/183 (4'-bromobenzoyl, 16), 175 (3), 157/155 (11), 147 ($M^+$-4'-bromobenzoyl, 100), 121 (11), 108 (8), 93 (15), 80 (7), 76 (11), 65 (18), 50 (13), 44 (46).

Example 4

3-(4'-Fluorobenzoyl)-3,4-dihydro-2H-8-methylpyrido[1,2-a]pyrimidinium perchlorate 1 mmol (243 mg) of 1-(4'-fluorophenyl)-2-(dimethylaminomethyl)prop-2-en-1-one hydrochloride and 1 mmol (108 mg) of 2-amino-4-methylpyridine (2-amino-4-picoline) were dissolved in 5 ml of water/ethanol (1:1 volume/volume) and refluxed for 1 hour. The solvent was removed under a vacuum (bath temperature 50° C.), the residue dissolved in 5 ml of 2-propanol, combined with cooling with 4 mmol of 70 vol. % perchloric acid and stirred for 30 min in the ice bath and the solvent removed under a vacuum. The oily residue was redissolved with 5 ml of 2-propanol and heated to boiling. The precipitate which arose on cooling was removed by suction filtration and dried under an oil pump vacuum (12 hours, 40° C.), Yield: 53 mg (0.14 mmol), 14% of theoretical, yellow crystals/yellow oil, $C_{16}H_{16}N_2O_5FCl$ (370.76)

$^1$H-NMR (300 MHz, DMSO-$d_6$):

δ/ppm (TMS)=2.31 (s, 3H, $CH_3$), 3.50 (mc, 1H, H-2/4), 3.73 (mc, 1H, H-2/4), 4.28-4.52 (m, 3H, H-3, H-2/4), 6.72-6.76 (m, 2H, H-7/9), 7.40 (mc, 2H, ArH), 7.90 (mc, 1H, H-6), 8.18 (mc, 2H, ArH), 9.22 (s, br, NH).

MS (EI, MeOH):

m/z(%)=271 ($M^+$+1 of the base, 1), 270 ($M^+$, 5), 269 ($M^+$−1, 4), 254 (1), 239 (3), 222 (4), 195 (3), 90 (6), 181 (2), 155 (4), 147 ($M^+$-4'-fluorobenzoyl, 42), 135 (6), 127 (6), 123 (4'-fluorobenzoyl, 34), 121 (10), 108 (28), 95 (34), 80 (28), 65 (16), 58 (100), 44 (52).

Example 5

3-Benzoyl-3,4-dihydro-2H-8-methylpyrido[1,2-a]pyrimidinium perchlorate 1 mmol (225.7 mg) of 1-phenyl-2-(dimethylaminomethyl)prop-2-en-1-one hydrochloride and 1 mmol (108 mg) of 2-amino-4-methylpyridine (2-amino-4-picoline) were dissolved in 5 ml of ethanol/water (1/1 volume/volume) and refluxed for 1 hour. The solvent was removed under a vacuum (bath temperature 50° C.), the residue was dissolved in 3 ml of 2-propanol and cooled (ice/water/sodium chloride). A precipitate was then obtained at low temperature by precipitation by dropwise addition of a mixture of 70 vol. % perchloric acid and 2-propanol (1/1 volume/volume) and stirring for 30 min in the ice bath. The supernatant solution was removed and the precipitate stirred for 30 min in 10 ml of 2-propanol at 0° C., the supernatant solution was decanted, recrystallised from methanol and the residue dried under an oil pump vacuum at 60° C.

Yield: 204 mg (0.58 mmol) 58% of theoretical, light yellow crystals,

Melting point: >290° C.

$C_{16}H_{17}N_2O_5Cl$ (352.77)

Calculated: C 54.47; H 4.86; N 7.94;

Found: C 54.65; H 4.95; N 7.79;

$^1$H-NMR (300 MHz, DMSO-$d_6$):

δ/ppm (TMS)=2.29 (s, br, 3H, $CH_3$), 3.51 (mc, 1H, H-2/4), 3.74 (mc, 1H, H-2/4), 4.34-4.51 (m, 3H, H-3, H-2/4), 6.71 (dd, 1H, $^3J$=6.8, $^4J$=1.7, H-7), 6.79 (s, 1H, H-9), 7.57 (mc, 2H, H-3'/5'), 7.70 (t, 1H, $^3J$=7.4, H-4'), 7.90 (d, 1H, $^3J$=6.8, H-6), 8.04 (d, 2H, $^3J$=7.3, H-2'/6'), 9.38 (s, br, NH).

MS (EI, MeOH):

m/z (%)=252 ($M^+$ of the base, 21), 251 ($M^+$−1, 1), 188 (3), 177 (2), 172 (17), 160 (1), 147 ($M^+$-benzoyl, 7), 135 (2), 131 (2), 121 (2), 112 (3), 108 (31) 105 (benzoyl, 14), 92 (2), 80 (24), 77 (14), 66 (4), 58 (100), 51 (7), 44 (32), 42 (13).

Example 6

3-Benzoyl-3,4-dihydro-2H-6,8-dimethylpyrido[1,2-a]pyrimidinium perchlorate 1 mmol (225.7 mg) of 1-phenyl-2-(dimethylaminomethyl)prop-2-en-1-one hydrochloride and 1 mmol (122 mg) of 2-amino-4,6-dimethylpyridine were dissolved in 5 ml of ethanol/water (1/1 volume/volume) and refluxed for 1 hour. The solvent was removed under a vacuum (bath temperature 50° C.), the residue was dissolved in 3 ml of 2-propanol and cooled (ice/water/sodium chloride). A precipitate was then obtained at low temperature by precipitation by dropwise addition of a mixture of 70 vol. % perchloric acid and 2-propanol (1/1 volume/volume) and stirring for 30 min in the ice bath. The supernatant solution was removed and the precipitate stirred for 30 min in 10 ml of 2-propanol at 0° C., the supernatant solution was decanted, recrystallised from methanol and the residue dried under an oil pump vacuum at 40° C.

Yield: 120 mg (0.32 mmol) 32% of theoretical, colourless crystals,

Melting point: 78° C.

$C_{17}H_{19}N_2O_5Cl$ (366.80)

Calculated: C 55.67; H 5.22; N 7.63;

Found: C 55.83; H 5.31; N 7.50;

$^1$H-NMR (300 MHz, DMSO-$d_6$):

δ/ppm (TMS)=2.27 (s, br, 3H, $CH_3$), 2.47 (s, br, 3H, $CH_3$), 3.41-3.47 (m, 1H, H-2/4), 3.73-3.82 (m, 1H, H-2/4), 4.29-4.42 (m, 3H, H-3, H-2/4), 6.69 (s, br, 2H, H-7/9), 7.62 (mc, 2H, H-3'/5'), 7.73 (mc, 1H, H-4'), 8.08 (d, 1H, $^3J$=8.4, H-2'/6'), 9.28 (s, br, NH).

MS (EI, MeOH):

m/z (%)=267 ($M^+$+1 of the base, 1), 266 ($M^+$, 6), 265 ($M^+$−1, 8), 236 (2), 223 (2), 197 (2), 176 (6), 172 (13), 161 ($M^+$-benzoyl, 66), 149 (10), 135 (13), 122 (34), 112 (2), 105 (benzoyl, 56), 94 (15), 91 (11), 77 (60), 65 (5), 58 (100), 51 (21), 44 (52).

Example 7

3-(4'-Chlorobenzoyl)-3,4-dihydro-2H-8-methylpyrido[1,2-a]pyrimidinium perchlorate 1 mmol (260 mg) of 1-(4'-chlorophenyl)-2-(dimethylaminomethyl)prop-2-en-1-one hydrochloride and 1 mmol (108 mg) of 2-amino-4-methylpyridine (2-amino-4-picoline) were dissolved in 5 ml of ethanol/water (1/1 volume/volume) and refluxed for 1 hour. The solvent was removed under a vacuum (bath temperature 50° C.), the residue was dissolved in 3 ml of 2-propanol and cooled (ice/water/sodium chloride). A precipitate was then obtained at low temperature by precipitation by dropwise addition of a mixture of 70 vol. % perchloric acid and 2-propanol (1/1 volume/volume) and stirring for 30 min in the ice bath. The supernatant solution was removed and the precipitate stirred for 30 min in 10 ml of 2-propanol at 0° C., the supernatant solution was decanted, recrystallised from methanol and the residue dried under an oil pump vacuum at 60° C.

Yield: 186 mg (0.47 mmol), 47% of theoretical, light yellow crystals,

Melting point: 123-125° C.

$C_{16}H_{16}N_2O_5Cl_2$ (387.22)

Calculated: C 49.63; H 4.17; N 7.23;

Found: C 49.77; H 4.26; N 7.11;

$^1$H-NMR (300 MHz, DMSO-$d_6$):

δ/ppm (TMS)=2.31 (s, br, 3H, $CH_3$), 3.52 (mc, 1H, H-2/4), 3.73-3.81 (m, 1H, H-2/4), 4.35-4.81 (m, 3H, H-3, H-2/4), 6.74 (d, 1H, $^2J$=6.9, B-7), 6.78 (s, 1H, H-9), 7.67 (d, 2H, 3J=8.6, H-3'/5'), 7.90 (d, 1H, $^3J$=6.9, H-6), 8.08 (d, 2H, 3J=8.6, H-2'/6'), 9.27 (s, br, NH).

MS (EI, MeOH):

m/z (%)=287 ($M^+$+1 of the base,4), 286 ($M^+$, 9), 285 ($M^+$−1, 13), 271 (2), 257 (2), 249 (1), 181 (2), 175 (3), 166 (3), 156 (7), 147 ($M^+$-chlorobenzoyl, 100), 145 (11), 141 (16), 139 (chlorobenzoyl, 48), 133 (6), 121 (12), 111 (29), 92 (26), 75 (15), 65 (21), 58 (11), 44 (34).

Example 8

3-(4'-Biphenylcarbonyl)-3,4-dihydro-2H-8-methylpyrido[1,2-a]pyrimidinium perchlorate 1 mmol (302 mg) of 1-biphenyl-2-(dimethylaminomethyl)prop-2-en-1-one hydrochloride and 1 mmol (108 mg) of 2-amino-4-methylpyridine (2-amino-4-picoline) were dissolved in 5 ml of water/ethanol (1/1 volume/volume) and refluxed for 1 hour. The solvent was removed under a vacuum (bath temperature 50° C.), the residue was dissolved in 8 ml of 2-propanol and cooled (ice/water/sodium chloride). A precipitate was then obtained at low temperature by precipitation by dropwise addition of a mixture of 70 vol. % perchloric acid and 2-propanol (1/1 volume/volume) and stirring for 30 min in the ice bath. The supernatant solution was removed and the precipitate stirred for 30 min in 10 ml of 2-propanol at 0° C., the supernatant solution was decanted, recrystallised from methanol and the residue dried under an oil pump vacuum at 60° C.

Yield: 258 mg (0.60 mmol) 60% of theoretical, light yellow crystals,

Melting point: 111° C.

$C_{22}H_{21}N_2O_5Cl$ (428.87)

Calculated: C 61.61; H 4.93; N 6.53;

Found: C 61.73; H 5.11; N 6.52;

$^1$H-NMR (300 MHz, DMSO-$d_6$):

δ/ppm (TMS)=2.33 (s, br, 3H, $CH_3$), 2.84-2.88 (m, 1H, H-2/4), 3.59 (mc, 1H, H-2/4), 4.39-4.56 (m, 3H, H-3, H-2/4), 6.67-6.78 (m, 2H, H-7, H-9), 7.43-7.56 (m, 3H, H-4", H-3"/5"), 7.78 (d, 2H, $^3J$=7.0, H-2"/6"), 7.92 (d, 2H, $^3J$=8.5, H-3'/5'), 7.94 (d, 1H, $^3J$=6.8, H-6), 8.16 (d, 2H, $^3J$=8.5, H-2'/6'), 9.20 (s, br, NH).

Example 9

3-(4'-Biphenylcarbonyl)-3,4-dihydro-2H-6-methylpyrido[1,2-a]pyrimidinium perchlorate 1 mmol (302 mg) of 1-biphenyl-2-(dimethylaminomethyl)prop-2-en-1-one hydrochloride and 1 mmol (108 mg) of 2-amino-6-methylpyridine (2-amino-6-picoline) were dissolved in 5 ml of water/ethanol (1/1 volume/volume) and refluxed for 1 hour. The solvent was removed under a vacuum (bath temperature 50° C.), the residue was dissolved in 3 ml of 2-propanol and cooled (ice/water/sodium chloride). A precipitate was then obtained at low temperature by precipitation by dropwise addition of a mixture of 70 vol. % perchloric acid and 2-propanol (1/1 volume/volume) and stirring for 30 min in the ice bath. The supernatant solution was removed and the precipitate stirred for 30 min in 10 ml of 2-propanol at 0° C., the supernatant solution was decanted, recrystallised from methanol and the residue dried under an oil pump vacuum at 60° C.

Yield: 156 mg (0.36 mmol) 36% of theoretical, light yellow crystals, $C_{22}H_{21}N_2O_5Cl$ (428.87)

Calculated: C 61.61; H 4.93; N 6.53;

Found: C 61.82; H 5.02; N 6.38;

$^1$H-NMR (300 MHz, DMSO-$d_6$):

δ/ppm (TMS)=2.5* (s, br, 3H, $CH_3$), 3.51 (mc, 1 H, H-2/4), 3.79 (mc, 1H, H-2/4), 4.35-4.55 (m, 3H, H-3, H-2/4), 6.81 (d, 1 H, $^3J$=7.0, H-7/9), 6.95 (d, 1 H, $^3J$=9.0, H-7/9), 7.42-7.55 (m, 3H, H-3"/5", H-4"), 7.70 (mc, 1H, H-8), 7.79 (d, 2H, $^3J$=7.0, H-2"/6"), 7.90 (d, 1H, $^3J$=8.4, H-3'/5'), 8.18 (d, 2H, $^3J$=8.4, H-2'/6'), 9.60 (s, br, NH).

(*) partially masked by DMSO signal

MS (EI, MeOH):

m/z (%)=329 ($M^+$+1 of the base, 2), 328 ($M^+$, 8), 327 ($M^+$−1, 8), 313 (1), 300 (1), 285 (2), 266 (1), 248 (2), 236 (3), 222 (1), 208 (5), 181 (4'-biphenylcarbonyl, 16), 167 (2), 152 (22), 147 ($M^+$-4'-biphenylcarbonyl, 100), 121 (13), 108 (11), 92 (23), 80 (6), 76 (5), 65 (16), 58 (10), 44 (11).

The following example compounds were produced in a similar manner to the above-described Examples:

Example 10

(4-Ethoxy-phenyl)-(8-methyl-3,4-dihydro-2H-pyrido[1,2-a]pyrimidin-3-yl)-methanone hydroperchlorate

Example 11

Biphenyl-4-yl-(6,8-dimethyl-3,4-dihydro-2H-pyrido[1,2-a]pyrimidin-3-yl)-methanone hydroperchlorate

Example 12

(8-Methyl-3,4-dihydro-2H-pyrido[1,2-a]pyrimidin-3-yl)-(6-methyl-naphthalen-2-yl)-methanone hydroperchlorate

Example 13

(6-Methoxy-naphthalen-2-yl)-(8-methyl-3,4-dihydro-2H-pyrido[1,2-a]pyrimidin-3-yl)-methanone hydroperchlorate Pharmacological Data The NOS and HTS-NOS assays were performed as described above.

Enzyme Preparation

Rat cerebella were used as the starting tissue. The animals were stunned and killed, the brain tissue, the cerebellum, was dissected out, 1 ml of enzyme preparation buffer (4° C.) was added per cerebellum, and the tissue was disrupted for 1 min at 6000 rpm in a Polytron homogeniser. The mixture was then centrifuged at 4° C. for 15 min at 20,000 g, and the supernatant was then decanted off and frozen in portions at −80° C., discarding the precipitate. The frozen supernatant was subsequently thawed for the assay and pipetted out onto a microtitre plate.

Incubation Batch:

96-well MTPs with a well capacity of <250 μl were used. The pipetting sequence is shown in Table 1 below:

TABLE 1

| Substance | Molarity (in batch) | Volume: | *Protein (in batch) |
|---|---|---|---|
| 1. Incubat. buffer | — | 100 μl | — |

TABLE 1-continued

| Substance | Molarity (in batch) | Volume: | *Protein (in batch) |
|---|---|---|---|
| 2. Compound to be tested according to Examples 1-9 | variable; preferably $10^{-5}$ M | variable; preferably 20 μl | — |
| 3. NADPH | 0.5 mM | 20 μl | — |
| 4. Enzyme | — | variable; maximum volume of enzyme solution 50 μl | variable; maximum usable quantity of protein = 100 μg |
| 5. [$^3$H] substrate | variable; preferably 50 nM | variable; preferably 10 μl | — |
| Final volume: | | max. 250 μl | |

*Protein determination was performed in accordance with O. H. Lowry et al.; J. Biol. Chem. 193, 265 (1951). The corresponding literature description is hereby introduced as a reference and is deemed to be part of the disclosure.

Once pipetting was complete, a lid was placed on this MTP (assay MTP) and incubation performed at 25° C. (room temperature [RT]) for 5-60 min, depending on the quantity and activity of the enzyme used (see in this connection Table 1). The contents of the assay MTP were then transferred with the assistance of a 96-well cell harvester into a 96-well cation exchanger MTP (filter MTP), suction filtered and washed once with 200 ml of $H_2O$.

The plate was then dried for 1 hour at 60° C. in a drying cabinet and the bottom of the filter MTP was then carefully sealed from beneath with a "back seal". 35 μl of scintillating material were then pipetted into each well. The top of the plate was also sealed with a "top seal". After 1 hour's waiting time, the plate was assessed on the β-counter.

For the purposes of performing HTS, the incubation medium, NADPH and enzyme solution were combined before the beginning of the pipetting step so that it would not be necessary to carry out three separate time-consuming pipetting operations.

Materials Used

Arginine, L-[2,3,4-$^3$H]-monohydrochloride; item no. NET-1123, supplier NEN $CaCl_2$ anhydrous; item no. 2388.1000; supplier Merck KGaA 1,4-Dithiothreitol (DTT), item no. 708984; supplier ROCHE $Na_2$-EDTA dihydrate; item no. 03680; supplier FLUKA HEPES, item no. H-3375; supplier SIGMA NADPH, tetrasodium salt; item no. 1585363; supplier ROCHE TRIS; item no. 93349; supplier FLUKA Enzyme Preparation Buffer:

50 mM tris-HCl with 1 mM EDTA:

The pH value of the buffer was adjusted to 7.4 at 4° C.

Incubation Buffer (Medium):

50 mM HEPES with 1 mM EDTA; 1.25 mM $CaCl_2$ and 1 mM dithiothreitol.

The pH value of the buffer was adjusted to 7.4 at 25° C.

Washing Medium: $H_2O$

Inhibition of enzyme activity by the particular pyrido[1,2-a]pyrimidine compound according to Examples 1-9 is stated in Table 2 below as the $IC_{50}$ value or Inhibitory Concentration 50, which is the concentration at which enzyme activity is reduced by 50%.

TABLE 2

| Compound according to | NOS Arg IC$_{50}$ (µM) |
| --- | --- |
| Example 1: | 1.4 |
| Example 2: | 6.7 |
| Example 3: | 14 |
| Example 4: | 8.5 |
| Example 5: | 9.1 |
| Example 6: | 8.4 |
| Example 7: | 6.4 |
| Example 8: | 13 |
| Example 9: | 7.6 |

Formaldehyde Test (Rat):

The analgesic action of the compounds of the general formula II used according to the invention was determined as described above. The compounds investigated in each case exhibited moderate to strong inhibition of the formaldehyde-induced nociception.

The following Table shows the value for the substituted pyrido[1,2-a]pyrimidine compound according to Example 1:

TABLE 3

| Compound according to | ED$_{50}$ |
| --- | --- |
| 1 | 7.27 mg/kg i.v. |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A pyrido[1,2-a]pyrimidine compound corresponding to formula I

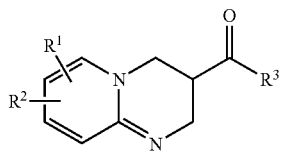

I wherein
R$^1$ and R$^2$, mutually independently, in each case denote hydrogen, halogen or a linear or branched, optionally at least monosubstituted, alkyl residue, and
R$^3$ denotes an optionally at least monosubstituted, monocyclic aryl or heteroaryl residue, which is optionally fused with an optionally at least monosubstituted monocyclic or polycyclic ring system optionally comprising at least one heteroatom as a ring member,
or a physiologically acceptable salt thereof,
provided that the following compounds are excluded:
compounds corresponding to formula I, wherein R$^1$ and R$^2$ denote hydrogen and a methyl residue or wherein R$^1$ and R$^2$ denote hydrogen and R$^3$ denotes a phenyl residue which is unsubstituted or monosubstituted with a methyl residue, methoxy residue, Cl or Br, and their hydroperchlorate salts, and the following compounds and their hydroperchlorate salts:

(3,4-dihydro-9-methyl-2H-pyrido[1,2-a]pyrimidin-3-yl) (3,4-dimethoxyphenyl)-methanone, (3,4-dihydro-6-methyl-2H-pyrido[1,2-a]pyrimidin-3-yl) (3,4-dimethoxyphenyl)-methanone, (3,4-dihydro-2H-pyrido[1,2-a]pyrimidin-3-yl)(3,4-dimethoxyphenyl)-methanone and (3,4-dichlorophenyl)(3,4-dihydro-2H-pyrido[1,2-a]pyrimidin-3-yl)-methanone.

2. A compound according to claim 1, wherein said compound is present in the form of a free base.

3. A compound according to claim 1, wherein said compound is present in the form of a pure enantiomer or pure diastereoisomer.

4. A compound according to claim 1, wherein said compound is present in the form of a mixture of stereoisomers.

5. A compound according to claim 1, wherein said compound is present in the form of a racemic mixture.

6. A compound according to claim 1, wherein said compound is present in the form of a hydroperchorate salt.

7. A compound according to claim 1, wherein R$^1$ and R$^2$, mutually independently, in each case denote H, F, Cl, Br or a linear or branched, optionally at least monosubstituted, C$_{1-5}$ alkyl residue.

8. A compound according to claim 1, wherein R$^1$ and R$^2$, mutually independently, denote H or a methyl residue.

9. A compound according to claim 1, wherein R$^3$ denotes an optionally at least monosubstituted, 5- or 6-membered, monocyclic aryl or heteroaryl residue which is optionally fused with an optionally at least monosubstituted mono-, di- or tricyclic ring system optionally comprising at least one heteroatom as a ring member, wherein the rings of the ring system are in each case 5- to 7-membered.

10. A compound according to claim 9, wherein said monocyclic aryl or heteroaryl residue is fused with an at least monosubstituted phenyl residue or an optionally at least monosubstituted phenyl, naphthyl, furanyl, thiophenyl, pyrrolyl, imidazolyl, pyrazolyl, pyridinyl, pyrimidinyl, quinolinyl or isoquinolinyl residue.

11. A compound according to claim 1, wherein said compound is selected from the group consisting of:

3-(2'-naphthoyl)-3,4-dihydro-2H-8-methylpyrido[1,2-a] pyrimidine, 3-(2'-naphthoyl)-3,4-dihydro-2H-6,8-dimethylpyrido[1,2-a]pyrimidine, 3-(4'-fluorobenzoyl)-3,4-dihydro-2H-8-methylpyrido[1,2-a]pyrimidine, 3-benzoyl-3,4-dihydro-2H-6,8-dimethylpyrido[1,2-a]pyrimidine, 3-(4'-biphenylcarbonyl)-3,4-dihydro-2H-8-methylpyrido [1,2-a]pyrimidine, 3-(4'-biphenylcarbonyl)-3,4-dihydro-2H-6-methylpyrido [1,2-a]pyrimidine, (4-ethoxy-phenyl)-(8-methyl-3,4-dihydro-2H-pyrido[1,2-a]pyrimidin-3-yl)-methanone, biphenyl-4-yl-(6,8-dimethyl-3,4-dihydro-2H-pyrido[1,2-a]pyrimidin-3-yl)-methanone, (8-methyl-3,4-dihydro-2H-pyrido[1,2-a]pyrimidin-3-yl)-(6-methyl-naphthalen-2-yl)-methanone, (6-methoxy-naphthalen-2-yl)-(8-methyl-3,4-dihydro-2H-pyrido [1,2-a]pyrimidin-3-yl)-methanone and physiologically acceptable salts thereof.

12. A compound according to claim 11, wherein said compound is in the form of a hydroperchlorate salt.

13. A process for producing a substituted pyrido[1,2-a]pyrimidine compound according to claim 1, comprising:
reacting at least one compound corresponding to formula III,

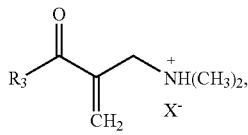

wherein X⁻ denotes a chloride or bromide anion, with at least one compound corresponding to formula IV,

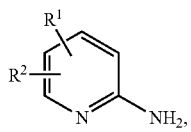

in a suitable reaction medium, with heating.

14. The process of claim 13, wherein said reaction medium comprises a water and alcohol mixture.

15. The process of claim 13, wherein said reaction medium comprises a water and ethanol mixture.

16. The process of claim 13, further comprising causing refluxing.

17. The process of claim 13, further comprising isolating the resultant compound corresponding to formula I.

18. A pharmaceutical formulation comprising at least one substituted pyrido[1,2-a]pyrimidine compound corresponding to formula II

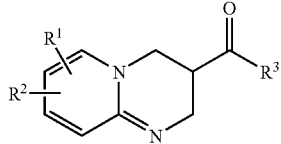

wherein
$R^1$ and $R^2$, mutually independently, in each case denote hydrogen, halogen or a linear or branched, optionally at least monosubstituted, alkyl residue, and
$R^3$ denotes an optionally at least monosubstituted, monocyclic aryl or heteroaryl residue, which is optionally fused with an at least monosubstituted monocyclic or polycyclic ring system optionally comprising at least one heteroatom as a ring member or a physiologically acceptable salt thereof.

19. The pharmaceutical formulation of claim 18, wherein said compound is present in the form of a free base.

20. The pharmaceutical formulation of claim 18, wherein said compound is present in the form of a pure enantiomer or pure diastereoisomer.

21. The pharmaceutical formulation of claim 18, wherein said compound is present in the form of a mixture of stereoisomers.

22. The pharmaceutical formulation of claim 18, wherein said compound is present in the form of a racemic mixture.

23. The pharmaceutical formulation of claim 18, wherein said compound is present in the form of a hyperchorate salt.

24. The pharmaceutical formulation of claim 18, wherein the residues $R^1$ and $R^2$, mutually independently, in each case denote H, F, Cl, Br or a linear or branched, optionally at least monosubstituted $C_{1-6}$ alkyl residue.

25. The pharmaceutical formulation of claim 18, wherein the residues $R^1$ and $R^2$, mutually independently, in each case denote H or a methyl residue.

26. The pharmaceutical formulation of claim 18, wherein the residue $R^3$ denotes an optionally at least monosubstituted 5- or 6-membered, monocyclic aryl or heteroaryl residue which is optionally an, at least monosubstituted, 5- or 6-membered ring.

27. A pharmaceutical formulation according to claim 26, wherein the monocyclic aryl or heteroaryl residue of $R^3$ is an optionally at least monosubstituted 5- or 6-membered ring, which is fused with an optionally at least monosubstituted, mono-, di- or tricyclic ring system optionally comprising at least one heteroatom as a ring member, wherein the rings of the ring system are in each case 5- to 7-membered.

28. A pharmaceutical formulation according to claim 27, wherein the rings of the ring system are in each case, an optionally at least monosubstituted phenyl, naphthyl, furanyl, thiophenyl, pyrrolyl, imidazolyl, pyrazolyl, pyridinyl, pyrimidinyl, quinolinyl or isoquinolinyl residue.

29. A pharmaceutical formulation according to claim 27, wherein the rings of the ring system are, an optionally at least monosubstituted phenyl or naphthyl residue.

30. A pharmaceutical formulation according to claim 18, wherein the compound corresponding to formula II is selected from the group consisting of:
3-(2'-naphthoyl)-3,4-dihydro-2H-8-methylpyrido[1,2-a]pyrimidine,
3-(2'-naphthoyl)-3,4-dihydro-2H-6,8-dimethylpyrido[1,2-a]pyrimidine,
3-(4'-fluorobenzoyl)-3,4-dihydro-2H-8-methylpyrido[1,2-a]pyrimidine,
3-benzoyl-3,4-dihydro-2H-6,8-dimethylpyrido[1,2-a]pyrimidine,
3-(4'-biphenylcarbonyl)-3,4-dihydro-2H-8-methylpyrido[1,2-a]pyrimidine,
3-(4'-biphenylcarbonyl)-3,4-dihydro-2H-6-methylpyrido[1,2-a]pyrimidine,
3-(4'-bromobenzoyl)-3,4-dihydro-2H-8-methylpyrido[1,2-a]pyrimidine,
3-(4'-chlorobenzoyl)-3,4-dihydro-2H-8-methylpyrido[1,2-a]pyrimidine,
3-benzoyl-3,4-dihydro-2H-8-methylpyrido[1,2-a]pyrimidine,
(4-ethoxy-phenyl)-(8-methyl-3,4-dihydro-2H-pyrido[1,2-a]pyrimidin-3-yl)-methanone,
biphenyl-4-yl-(6,8-dimethyl-3,4-dihydro-2H-pyrido[1,2-a]pyrimidin-3-yl)-methanone,
(8-methyl-3,4-dihydro-2H-pyrido[1,2-a]pyrimidin-3-yl)-(6-methyl-naphthalen-2-yl)-methanone,
(6-methoxy-naphthalen-2-yl)-(8-methyl-3,4-dihydro-2H-pyrido[1,2-a]pyrimidin-3-yl)-methanone,
and physiologically acceptable salts thereof.

31. A method of treating or inhibiting a condition selected from the group consisting of migraine and pain, or for inhibiting nitrogen monoxide synthase (NOS), said method comprising administering a pharmaceutically effective amount of a pharmaceutical preparation according to claim 18.

32. The method of claim 31, wherein said pain is chronic pain or inflammatory pain.

* * * * *